(12) United States Patent
Tharaux et al.

(10) Patent No.: US 10,034,868 B2
(45) Date of Patent: Jul. 31, 2018

(54) METHODS FOR THE PREVENTION AND THE TREATMENT OF RAPIDLY PROGRESSIVE GLOMERULONEPHRITIS

(71) Applicants: INSERM (INSTITUT NATIONAL DE LA SANTÉ ET DE LA RECHERCHE MÉDICALE), Paris (FR); UNIVERSITÉ PARIS DESCARTES, Paris (FR); CENTRE HOSPITALIER DE L'UNIVERSITE DE MONTREAL, Montréal (Québec) (CA)

(72) Inventors: Pierre-Louis Tharaux, Paris (FR); Carole Henique Greciet, Créteil (FR); Guillaume Bollee, Montréal (CA)

(73) Assignees: INSERM (INSTITUT NATIONAL DE LA SANTÉ ET DE LA RECHERCHE MÉDICALE), Paris (FR); UNIVERSITÉ PARIS DESCARTES, Paris (FR)

(*) Notice: Subject to any disclaimer, the term of this patent is extended or adjusted under 35 U.S.C. 154(b) by 0 days.

(21) Appl. No.: 15/523,726

(22) PCT Filed: Nov. 4, 2014

(86) PCT No.: PCT/IB2014/002603
§ 371 (c)(1),
(2) Date: May 2, 2017

(87) PCT Pub. No.: WO2016/071727
PCT Pub. Date: May 12, 2016

(65) Prior Publication Data
US 2018/0036297 A1 Feb. 8, 2018

(51) Int. Cl.
*A61K 31/4439* (2006.01)
(52) U.S. Cl.
CPC .................. *A61K 31/4439* (2013.01)
(58) Field of Classification Search
CPC .................................... A61K 31/4439
USPC ........................................ 514/342
See application file for complete search history.

(56) References Cited

FOREIGN PATENT DOCUMENTS

GB    2 373 725 A    10/2002

OTHER PUBLICATIONS

Haraguchi et al., "Suppression of experimental crescentic glomerulonephritis by peroxisome proliferator-activated receptor (PPAR) [gamma] activators", Clinical and Experimental Nephrology, Mar. 1, 2003, pp. 27-32, vol. 7, No. 1, Japanese Society of Nephrology, Tokyo, JP.
Feng et al., "Clinicopathological characteristics and outcomes of patients with crescentic lupus nephritis", Kidney International, Apr. 29, 2009, pp. 307-317, vol. 76, No. 3.

*Primary Examiner* — Yevgeny Valenrod
(74) *Attorney, Agent, or Firm* — W&C IP

(57) ABSTRACT

The present invention relates to the prevention and the treatment of rapidly progressive glomerulonephritis.

5 Claims, 10 Drawing Sheets

Figure 1:
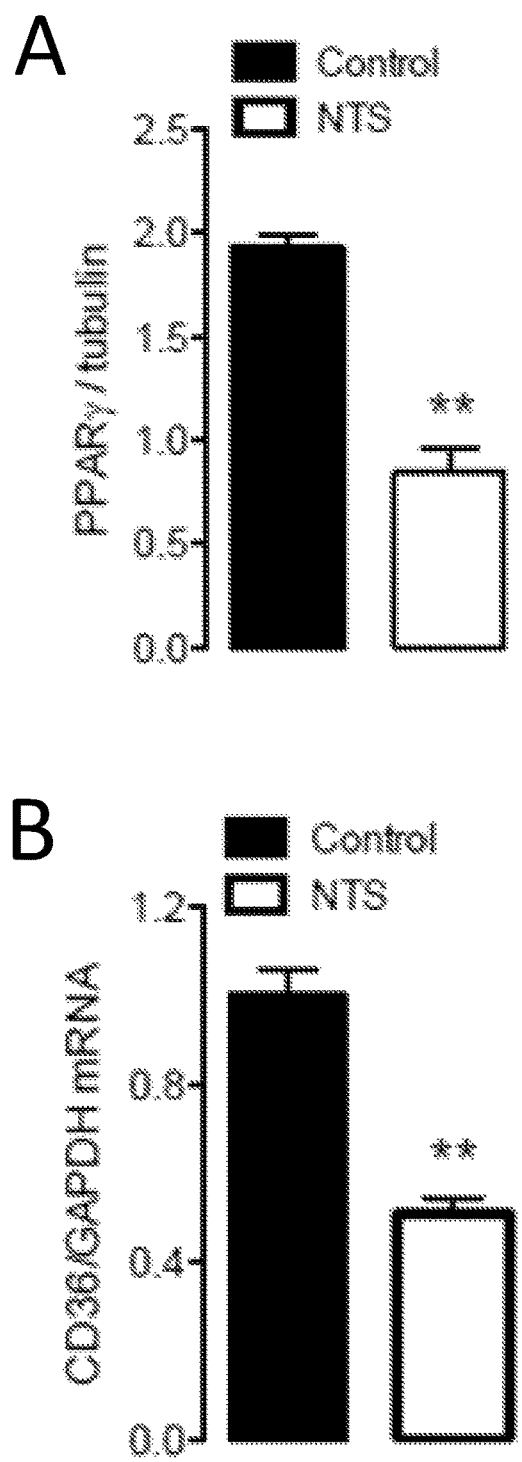

METHODS FOR THE PREVENTION AND THE TREATMENT OF RAPIDLY PROGRESSIVE GLOMERULONEPHRITIS

FIELD OF THE INVENTION

The present invention relates to the prevention and the treatment of rapidly progressive glomerulonephritis.

BACKGROUND OF THE INVENTION

Necrotizing and crescentic rapidly progressive glomerulonephritis (RPGN) results from a number of heterogeneous disease processes and has various clinical associations. However, all of these are characterized by crescentic glomerulonephritis on renal biopsy associated with a rapid decline in kidney function often necessitating long-term renalreplacement therapy if left untreated. Cellular crescents, defined as a multilayered accumulation of proliferating cells in Bowman's space, are pathognomonic of inflammatory glomerulonephritis. There are multiple causes of crescentic glomerulonephritis each leading to the irreversible loss of podocyte quiescence, aggravated endothelial injury, further damage to the glomerular filtration barrier, interrupts capillary blood flow, leading to irreversible ischemia and glomerular obsolescence. During crescent formation in mouse models of anti-glomerular basement membrane (GBM) RPGN, podocytes assume a migratory phenotype, attaching to the parietal basement membrane with their apical membrane where they proliferate for a limited period of time (Besse-Eschmann et al., 2004; Le Hir et al., 2001; Moeller et al., 2004). Recent data have confirmed that podocytes also contribute to crescent formation in man (Bariety et al., 2006; Thorner et al., 2008). Interestingly, in certain diseases such as IgA nephropathy or lupus nephritis, a classic immune complex-mediated renal disease, some of those affected develop severe crescentic glomerular lesions whereas others do not. Thus, one may hypothesize that in some instances local homeostatic mechanisms fail to maintain a quiescent phenotype in podocytes.

Accordingly, there is a need to develop new drugs that will be suitable for preventing or treating rapidly progressive glomerulonephritis (RPGN). In this way, it has been suggested that characterization of new compounds for treatment of RPGN may be highly desirable. Direct targeting of podocyte phenotype may help the glomerulus to withstand inflammatory stress and to prevent or stop the destructive process of crescent formation.

Peroxisome proliferator-activated receptor gamma (PPARγ) belongs to a group of nuclear receptors whose endogenous ligands include free fatty acids (FFAs) and eicosanoids. However, the best known PPARγ agonists are the thiazolidinediones (TZDs) (Ahmadian et al., 2013; Heikkinen et al., 2007). When activated, the PPARγ binds to DNA in complex with the retinoid X receptor (RXR), another nuclear receptor, increasing or decreasing the transcription of a number of specific genes. Although no PPARγ expression has been reported in whole human glomeruli (http://www.proteinatlas.org/ENSG00000132170/tissue/kidney), cultured podocytes constitutively express Pparγ mRNA which decreases upon the addition of puromycin aminonucleoside (PAN) (Kanjanabuch et al., 2007). Furthermore, pioglitazone, a TZD pharmacological agonist of PPARγ, increases both Ppar-γ mRNA and activity in cultured podocytes (Kanjanabuch et al., 2007). PPARγ stimulation is also effective in preventing podocyte injury in rats following the acute administration of PAN. (Zuo et al., 2012). Although the PAN model does not closely reflect any human disease TZDs have been shown to reduce albuminuria and glomerular injury in both mouse and rat models of diabetic nephropathy (Buckingham et al., 1998; Calkin et al., 2006; Cha et al., 2007; Ma et al., 2001; Yang et al., 2006). TZDs also have antiproteinuric effects in diabetic patients (Nakamura et al., 2001; Sarafidis et al., 2010). Finally, the improvement of glomerular injury by PPARγ agonism has been associated with reduced mitochondrial injury and oxidative stress in rat models of non-diabetic glomerulosclerosis such as aging-related sclerosis (Yang et al., 2009), 5/6 nephrectomy (Ma et al., 2001) and doxorubicin-induced focal and segmental glomerulosclerosis (Liu et al., 2010).

The mechanism of renoprotection conferred by PPARγ agonism is multifactorial. Antifibrotic and anti-inflammatory effects, suppression of the renin-angiotensin system, vascular protective and anti-apoptotic effects have all been proposed (Yang et al., 2012). In fact, TZDs pleiotropic actions may be effective in various cell types such as resident glomerular cells and immune cells. To date there has been no study of the glomerular PPARγ pathway in acute, severe inflammatory glomerulonephritis. This is likely due to the major focus on suppression of those aspects of the immune system mediating injury in autoimmune vasculitis rather than those promoting tissue tolerance to injury. Accordingly, most current therapeutic approaches to RPGN target the immune system (Henique et al., 2014). The current invention aimed to evaluate the proof of principle that delayed TZD administration could treat potentially lethal experimental RPGN.

Insight into the actions of PPARγ in non-immune cells was gained with podocyte-specific PPARγ loss of function in a severe model of RPGN. As pathway analysis from glomeruli of mice with RPGN and from primary podocytes suggested a potential association between PPARγ abundance and NF-E2-related factor 2 (Nrf2) transcriptional activity, the inventors went on to assess the role of Nrf2 in experimental RPGN. In experimental RPGN, Nrf2 deficient mice were phenotypically identical to mice with podocyte-specific PPARγ deficiency. These results indicate that the Nrf2-PPARγ axis is essential for maintaining podocyte tolerance to immune injury and could be a novel target for the treatment of necrotizing and crescentic RPGN.

There is no disclosure in the art of the role of PPARγ and Nrf2-PPARγ axis in rapidly progressive glomerulonephritis (RPGN), and the use of PPARγ agonists or PPARγ expression activators in the prevention or treatment of RPGN.

SUMMARY OF THE INVENTION

The present invention relates to the prevention and the treatment of rapidly progressive glomerulonephritis.

Particularly, the present invention relates to a compound which is selected from the group consisting of PPARγ agonist or PPARγ expression activator for use in the prevention or treatment of rapidly progressive glomerulonephritis (RPGN) in a subject in need thereof.

DETAILED DESCRIPTION OF THE INVENTION

The role of PPARγ in crescentic rapidly progressive glomerulonephritis (RPGN) was investigated by the inventors using glomerular podocytes in experimental RPGN, mouse model for RPGN, mouse model for doxorubicin-induced nephropathy and thiazolidinedione (TZD) systemic administration in RPGN mice. The inventors observed marked loss of peroxisome proliferator-activated receptor gamma (PPARγ) abundance and transcriptional activity in the glomerular podocytes in experimental RPGN. Podocyte specific Ppary gene targeting accentuated glomerular demolition with increased urinary loss of albumin and severe kidney failure. The inventors also demonstrated that PPARγ gain of function approach with thiazolidinedione (TZD) systemic administration failed to prevent severe RPGN in mice with podocyte specific Ppary gene deficiency. Loss of PPARγ in podocytes was already present at baseline in nuclear factor erythroid 2-related factor 2 (NRF2) deficient mice. NRF2 deficiency markedly aggravated the course of RPGN, an effect that was partially prevented by TZD administration, demonstrating a functional NRF2-PPARγ protective cascade. Furthermore, TZD delayed administration initiated after the onset of RPGN still alleviated the severity of experimental RPGN. These findings establish a requirement for the NRF2-PPARγ actions in podocytes, and demonstrated that these transcription factors have a role in augmenting the tolerance of glomeruli to severe immune-complex mediated injury.

Accordingly, the present invention relates to a compound which is selected from the group consisting of PPARγ agonist or PPARγ expression activator for use in the prevention or treatment of rapidly progressive glomerulonephritis (RPGN) in a subject in need thereof.

As used herein, the term "subject" denotes a mammal. In a preferred embodiment of the invention, a subject according to the invention refers to any subject (preferably human) afflicted with or susceptible to be afflicted with rapidly progressive glomerulonephritis (RPGN).

As used herein, the term "rapidly progressive glomerulonephritis" or "RPGN" has its general meaning in the art and refers to crescentic rapidly progressive glomerulonephritis, the glomerular injury that manifests as a proliferative histological pattern with accumulation of inflammatory cells and proliferation of intrinsic glomerular cells in Bowman's space ("crescents") and rapid deterioration of renal function. The term "Rapidly Progressive Glomerulonephritis" relates to crescentic glomerulonephritis or necrotizing crescentic glomerulonephritis or extracapillary glomerulonephritis (Jenette J C and Thomas D B. Crescentic glomerulonephritis. Nephrol Dial Transplant. 2001; 16 Suppl 6:80-2; Moeller M J, Soofi A, Hartmann I, et al. Podocytes populate cellular crescents in a murine model of inflammatory glomerulonephritis. J Am Soc Nephrol 2004; 15:61-67; Tarzi R M, Cook H T, Pusey C D. Crescentic glomerulonephritis: new aspects of pathogenesis. Semin Nephrol. 2011 July; 31(4):361-8; King S K, Jeansson M, Quaggin S E et al. New insights into the pathogenesis of cellular crescents. Current Opinion in Nephrology and Hypertension 2011, 20:258-262; Robert M. Kliegman, Md., Bonita M. D. Stanton, Md., Joseph St. Geme, Nina Schor and Richard E. Behrman, Md. Chapter 510—Rapidly Progressive (Crescentic) Glomerulonephritis. Nelson Textbook of Pediatrics, 19th Edition—Saunders Title, ISBN: 978-1-4377-0755-7).

RPGN can be primary or secondary. Secondary forms occur in any form of severe glomerulonephritis including membranoproliferative GN, IgA nephropathy, post infectious GN, anti-neutrophil cytoplasmic autoantibody (ANCA)-associated vasculitides, and systemic lupus erythematous (SLE).

As used herein, the term "PPARγ" has its general meaning in the art and refers to the PPAR gamma or PPARG, transcriptional factors belonging to the ligand-activated nuclear receptor superfamily. The term "PPARγ" also refers to Peroxisome proliferator-activated receptor gamma also known as the glitazone receptor, or NR1C3 (nuclear receptor subfamily 1, group C, member 3). PPARγ is a type II nuclear receptor that is encoded by the PPARG gene (Kota et al., 2005).

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include messenger RNAs which are modified, by processes such as capping, polyadenylation, methylation, and editing, and proteins (e.g., phosphatidylserine receptor) modified by, for example, methylation, acetylation, phosphorylation, ubiquitination, SUMOylation, ADP-ribosylation, myristilation, and glycosylation.

An "activator of expression" refers to a natural or synthetic compound that has a biological effect to activate the expression of a gene.

The term "PPARγ agonist" has its general meaning in the art and refers to a compound that selectively activates the PPARγ. The term "PPARγ agonist" refers to any compound that can directly or indirectly stimulate the signal transduction cascade related to the PPARγ. As used herein, the term "selectively activates" refers to a compound that preferentially binds to and activates PPARγ with a greater affinity and potency, respectively, than its interaction with the other sub-types or isoforms of the PPAR family (PPARα (alpha), PPARβ (beta) or PPARδ (Delta)). Compounds that prefer PPARγ, but that may also activate other PPAR sub-types, as partial or full agonists, and thus that may have multiple PPAR activities, are contemplated. Typically, a PPARγ agonist is a small organic molecule or a peptide.

Tests and assays for determining whether a compound is a PPARγ agonist are well known by the skilled person in the art such as described in Lehmann et al., Journal of Biological Chem., 270, 12953-12956 (1995) and Kota et al., 2005.

In one embodiment of the invention, the compound which is a PPARγ agonist may be a molecule, or a mixture of agents containing such a molecule (e.g. a botanical extract), that directly interacts with the PPARγ protein, and stimulates its interaction with retinoid X receptors and/or its target genes, to produce a physiological effect.

Agonists of PPARγ include, but are not limited to rosiglitazone, ciglitazone troglitazone, englitazone, pioglitazone, linoleic acid metabolites of linoleic, NSAIDs (such as ibuprofen) and indoles and arachidonic acid, and the mixtures thereof.

In one embodiment, the compound which is a PPARγ agonist may be an agent selected from the drug class of thiazolidinediones (TZDs) such as Rosiglitazone, Pioglitazone, Troglitazone, Isaglitazone, KRP297 (Murphy and Holer., 2000), 5-(4-[2-(N-methyl-N-(2-pyridyl) amino) ethoxy] benzyl)-2,4 thiazolidinedione (J. Biol. Chem., 270, 12963-12966; EP 0306228). Particular examples of thiazolidinediones are those disclosed in EP 0306228 and WO94/05659. Further particular examples are the thiazolidene-diones disclosed in EP0139421 and U.S. Pat. No. 5,478,852.

In one embodiment, the compound which is a PPARγ agonist may be a thiazolidinediones (such as thiazolidine-2,4diones) and moieties described, for example, in WO 02/49626.

A PPARγ agonist also includes non-thiazolidinedione agonists such as the compounds of formula (I) described in WO 97/31907 (or EP0888317), SB213068, SB219994, JTT501, GW1929, GW0072, L764406 (Murphy and Holer., 2000). A particular compound is 2 (S)-(2-benzoyl-phenylamino)-3-{4-[2-5-methyl-2-phenyl-oxazol-4-yl)-ethoxy]-phenyl}-propionic acid).

In one embodiment, the compound which is a PPARγ agonist may be a PPARy agonists disclosed in European Patent Applications, Publication Numbers: 0306228, 0008203, 0139421, 0032128, 0428312, 0489663, 0155845, 0257781, 0208420, 0177353, 0319189, 0332331, 0332332, 0528734 and 0508740, International Patent Application, Publication Numbers 92/18501, 93/02079, 93/22445 and U.S. Pat. Nos. 4,687,777, 5,104,888 and 5,478,852, especially the specific example thereof. The contents of these publications are included herein by reference.

A PPARγ agonist also includes natural extracts or fractions which are activators of the PPARγ pathway such as Pulpactyl (an extract from *Artemisia abrotanum*), Einkorn (an extract from *Triticum monococcum*), Honokiol (an extract from *Magnolia officinalis*) and polyacetylenes (an extract from *Notopterygium incisum*) (Atanasov et al., 2013 a and Atanasov et al., 2013 b).

In a further aspect, the present invention relates to a method of screening a candidate compound for use as a drug for the prevention or treatment of rapidly progressive glomerulonephritis (RPGN) in a subject in need thereof, wherein the method comprises the steps of:
  providing a PPARγ, providing a cell, tissue sample or organism expressing a PPARγ,
  providing a candidate compound such as small organic molecule, peptide, polypeptide, non-peptide compound, peptide mimetics, metabolically and/or conformationally stabilized peptide analogs, derivatives or pseudo-peptides,
  measuring the PPARγ activity,
  and selecting positively candidate compounds that induce PPARγ activity.

The term "PPARγ activity" has its general meaning in the art and refers to the biological activity associated with the activation of the PPARγ resulting from its signal transduction cascade, and including any of the downstream biological effects resulting from the binding of the candidate compound to PPARγ that may be equal or higher than the biological effect resulting from the binding of the PPARγ to its natural ligands.

Preferably, measuring the PPARγ activity involves determining a Ki on the PPARγ cloned and transfected in a stable manner into a CHO cell line, measuring the expression of PPARγ target genes (such as cytokines, Resistin, ABCA1, and GLUT4) or measuring PPARγ and retinoid X receptor (RXR) heterodimerization in the present or absence of the candidate compound.

Tests and assays for screening and determining whether a candidate compound is a PPARγ agonist are well known in the art (Lehmann et al., Journal of Biological Chem., 270, 12953-12956 (1995) and Kota et al., 2005). In vitro and in vivo assays may be used to assess the potency and selectivity of the candidate compounds to induce PPARγ activity.

Activities of the candidate compounds, their ability to bind PPARγ and their ability to induce similar effects to those of thiazolidinediones may be tested using isolated cells expressing PPARγ, podocytes expressing PPARγ, CHO cell line cloned and transfected in a stable manner by the human PPARγ or other tissues expressing PPARγ.

Activities of the candidate compounds and their ability to bind to the PPARγ may be assessed by the determination of a Ki on the PPARγ cloned and transfected in a stable manner into a CHO cell line and measuring the expression of PPARγ target genes or measuring PPARγ and retinoid X receptor (RXR) heterodimerization in the present or absence of the candidate compound.

Cells, podocytes and other tissues expressing another receptor than PPARγ may be used to assess selectivity of the candidate compounds.

In one embodiment, the present invention relates to a compound which is selected from the group consisting of PPARγ agonist or PPARγ expression activator in combination with a compound which is selected from the group consisting of NRF2 agonist or NRF2 expression activator for use in the prevention or treatment of rapidly progressive glomerulonephritis (RPGN) in a subject in need thereof.

The term "NRF2" has its general meaning in the art and refers to Nuclear factor erythroid-2 related factor 2 or Nuclear Factor E2p45-Related Factor (Nrf2), a cap-and-collar basic leucine zipper transcription factor, regulates a transcriptional program that maintains cellular redox homeostasis and protects cells from oxidative insult (Rangasamy T, et al., J Clin Invest 114, 1248 (2004); Thimmulappa R K, et al. Cancer Res 62, 5196 (2002); So H S, et al. Cell Death Differ (2006)).

Nrf2 activators include, but are not limited to bardoxolone methyl and fumaric acid esters and compounds described in US20130158077. Nrf2 activators of the present invention may comprise a Michael addition acceptor, one or more fumaric acid esters, i.e. fumaric acid mono- and/or diesters which are selected from the group of monoalkyl hydrogen fumarate and dialkyl fumarate, such as monomethyl hydrogen fumarate, dimethyl fumarate, monoethyl hydrogen fumarate, and diethyl fumarate, furthermore ethacrynic acid, bardoxolone methyl (methyl 2-cyano-3,12-dioxooleana-1,9 (11)dien-28-oate), isothiocyanate such as sulforaphane, 1,2-dithiole-3-thione such as oltipraz, 3,5-di-tert-butyl-4-hydroxytoluene, 3-hydroxycoumarin, or a pharmacologically active derivative or analog of the aforementioned agents.

In another embodiment, the present invention relates to a method of preventing or treating rapidly progressive glomerulonephritis in a subject in need thereof, comprising the step of administering to said subject a compound which is selected from the group consisting of PPARγ agonist or PPARγ expression activator.

In one embodiment said PPARγ agonist is Pioglitazone.

Pharmaceutical Composition

The compound of the invention may be used or prepared in a pharmaceutical composition.

In one embodiment, the invention relates to a pharmaceutical composition comprising the compound of the invention and a pharmaceutical acceptable carrier for use in the prevention or treatment of rapidly progressive glomerulonephritis (RPGN) in a subject of need thereof.

Typically, the compound of the invention may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The compound of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

Pharmaceutical compositions of the invention may include any further agent which is used in the prevention or treatment of rapidly progressive glomerulonephritis (RPGN).

For example, the anti-RPGN therapy may include cyclophosphamide, plasmapheresis, anti-CD20 antibody, mycophenolate mofetil and corticosteroids such as methylprednisolone or prednisone.

In one embodiment, said additional active agents may be contained in the same composition or administrated separately.

In another embodiment, the pharmaceutical composition of the invention relates to combined preparation for simultaneous, separate or sequential use in the prevention and treatment of rapidly progressive glomerulonephritis (RPGN).

The invention also provides kits comprising the PPARγ agonist or PPARγ expression activator of the invention. Kits containing the PPARγ agonist or PPARγ expression activator of the invention find use in therapeutic methods.

Diagnostics Methods

A further aspect of the invention relates to a method of identifying a subject having or at risk of having or developing rapidly progressive glomerulonephritis (RPGN), comprising a step of measuring in a sample obtained from said subject the expression level or activation level of PPARγ.

The method of the invention may further comprise a step consisting of comparing the expression level or activation level of PPARγ in the sample with a control, wherein detecting differential in the expression level or activation level of the PPARγ between the sample and the control is indicative of subject having or at risk of having or developing a rapidly progressive glomerulonephritis (RPGN).

The control may consist in sample associated with a healthy subject not afflicted with rapidly progressive glomerulonephritis (RPGN) as negative control, or in a sample associated with a subject afflicted with rapidly progressive glomerulonephritis (RPGN) as a positive control.

In one embodiment, low expression level or activation level of PPARγ is indicative of subject having or at risk of having or developing a rapidly progressive glomerulonephritis (RPGN), and accordingly, high expression level or activation level of PPARγ is indicative of subject not having or at risk of having or developing a rapidly progressive glomerulonephritis (RPGN).

Analyzing the PPARγ expression level may be assessed by any of a wide variety of well-known methods for detecting expression of a transcribed nucleic acid or translated protein.

In a preferred embodiment, the PPARγ expression level is assessed by analyzing the expression of mRNA transcript or mRNA precursors, such as nascent RNA, of PPARγ gene. Said analysis can be assessed by preparing mRNA/cDNA from cells in a biological sample from a subject, and hybridizing the mRNA/cDNA with a reference polynucleotide. The prepared mRNA/cDNA can be used in hybridization or amplification assays that include, but are not limited to, Southern or Northern analyses, polymerase chain reaction analyses, such as quantitative PCR (TaqMan), and probes arrays such as GeneChip™ DNA Arrays (AFFYMETRIX).

Advantageously, the analysis of the expression level of mRNA transcribed from the gene encoding for PPARγ involves the process of nucleic acid amplification, e. g., by RT-PCR (the experimental embodiment set forth in U.S. Pat. No. 4,683,202), ligase chain reaction (Barany, 1991), self sustained sequence replication (Guatelli et al., 1990), transcriptional amplification system (Kwoh et al., 1989), Q-Beta Replicase (Lizardi et al., 1988), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

In another preferred embodiment, the PPARγ expression level is assessed by analyzing the expression of the protein translated from said gene. Said analysis can be assessed using an antibody (e.g., a radio-labeled, chromophore-labeled, fluorophore-labeled, or enzyme-labeled antibody), an antibody derivative (e.g., an antibody conjugate with a substrate or with the protein or ligand of a protein of a protein/ligand pair (e.g., biotin-streptavidin)), or an antibody fragment (e.g., a single-chain antibody, an isolated antibody hypervariable domain, etc.) which binds specifically to the protein translated from the gene encoding for PPARγ.

Said analysis can be assessed by a variety of techniques well known from one of skill in the art including, but not limited to, enzyme immunoassay (EIA), radioimmunoassay (RIA), Western blot analysis and enzyme linked immunoabsorbant assay (IA).

Analyzing the PPARγ activation level may be assessed by any of a wide variety of well-known methods (Lehmann et al., Journal of Biological Chem., 270, 12953-12956 (1995) and Kota et al., 2005).

In a preferred embodiment, the PPARγ activation level is assessed by analyzing the expression of PPARγ target genes (such as cytokines, Resistin, ABCA1, and GLUT4) or measuring PPARγ and retinoid X receptor (RXR) heterodimerization.

In one embodiment, the expression level or activation level of PPARγ in the sample may be compared with a reference value. The reference value can be a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. Preferably, the person skilled in the art may compare the PPARγ expression levels or activation levels (obtained according to the method of the invention) with a defined threshold value. In one embodiment of the present invention, the threshold value is derived from the PPARγ expression level or activation level (or ratio, or score) determined in a biological sample derived from one or more subjects having a rapidly progressive glomerulonephritis (RPGN). Furthermore, retrospective measurement of the PPARγ expression levels or activation level (or ratio, or scores) in properly banked historical subject samples may be used in establishing these threshold values.

The present invention also relates to a method of preventing or treating rapidly progressive glomerulonephritis (RPGN) in a subject in need thereof comprising the steps of:
  i) providing a sample from said subject,
  ii) determining the PPARγ expression level or activation level in the biological sample obtained at step i),
  iii) comparing said PPARγ expression level or activation level measured in step ii) with a control, wherein low PPARγ expression level or activation level is indicative of subject having a rapidly progressive glomerulonephritis (RPGN), and
  iv) treating said subject having or at risk of having a rapidly progressive glomerulonephritis (RPGN) with a compound which is selected from the group consisting of PPARγ agonists or PPARγ expression activators.

A further aspect of the invention relates to a method for monitoring the efficacy of a treatment for a rapidly progressive glomerulonephritis (RPGN) in a subject in need thereof.

Methods of the invention can be applied for monitoring the treatment (e.g., drug compounds) of the subject. For example, the effectiveness of an agent to affect the expression level or activation level of the PPARγ according to the invention can be monitored during treatments of subjects receiving rapidly progressive glomerulonephritis (RPGN) treatments.

The "rapidly progressive glomerulonephritis (RPGN) treatment" relate to any type of rapidly progressive glomerulonephritis (RPGN) therapy undergone by the rapidly progressive glomerulonephritis (RPGN) subjects previously to collecting the rapidly progressive glomerulonephritis (RPGN) tissue samples, including cyclophosphamide, plasmapheresis, anti-CD20 antibody, mycophenolate mofetil and corticosteroids such as methylprednisolone or prednisone.

Accordingly, the present invention relates to a method for monitoring the treatment of subject affected with a rapidly progressive glomerulonephritis (RPGN), said method comprising the steps consisting of:

i) diagnosis of rapidly progressive glomerulonephritis (RPGN) before said treatment by performing the method of the invention ii) diagnosis of rapidly progressive glomerulonephritis (RPGN) after said treatment by performing the method of the invention iii) and comparing the results determined a step i) with the results determined at step ii) wherein a difference between said results is indicative of the effectiveness of the treatment.

The invention will be further illustrated by the following figures and examples. However, these examples and figures should not be interpreted in any way as limiting the scope of the present invention.

FIGURES

FIG. 1: Glomerular PPARγ expression is decreased in crescentic glomerulonephritis.

(A) Quantification of western blot bands for PPARγ normalized to tubulin band intensity (means of 6 mice per group, of two independent experiments). (B) RT-PCR analysis of CD36 mRNA expression in glomerular extracts from control or NTS-challenged mice (means of 5 mice per group, of two independent experiments). ** $P<0.01$ vs. control mice.

Figure 2:
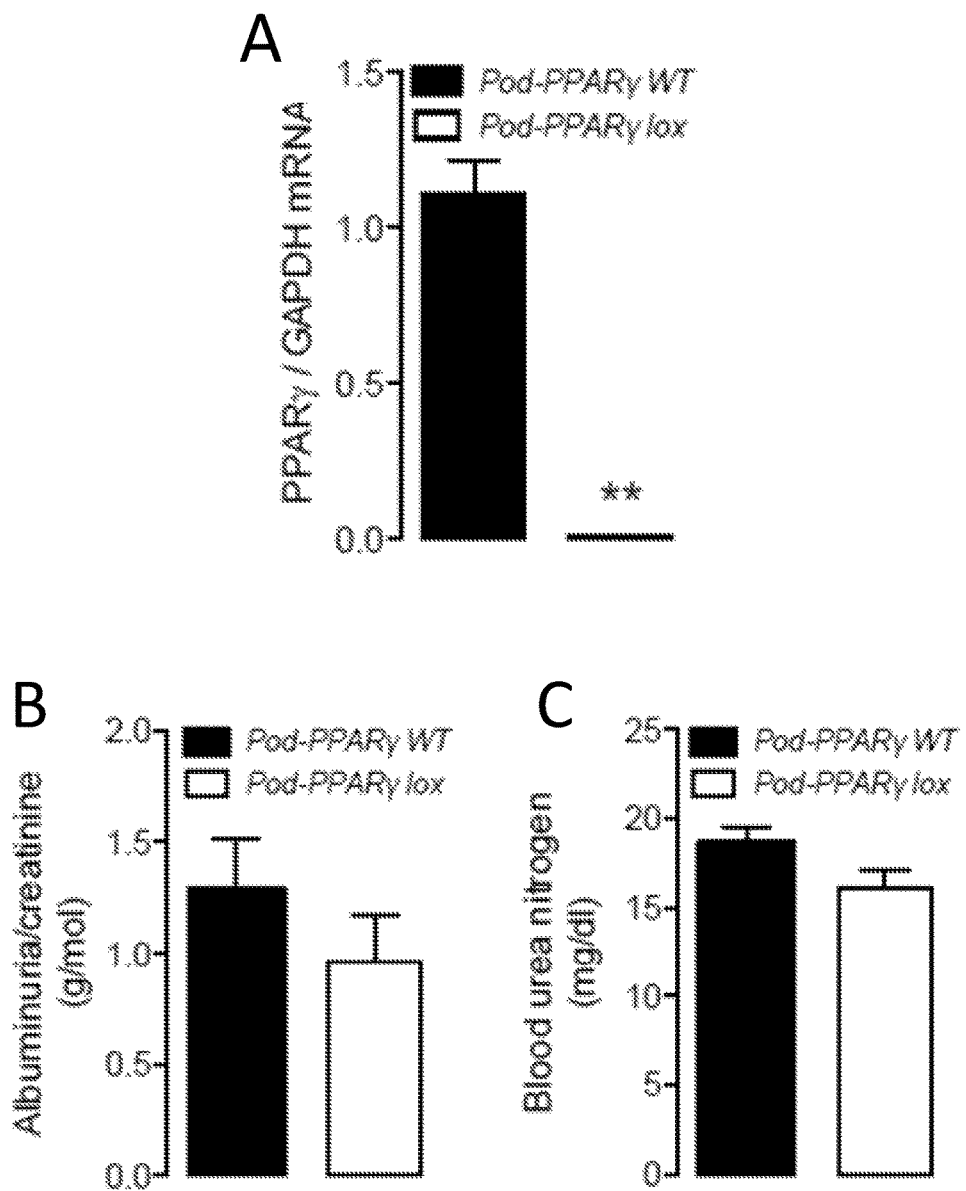

FIG. 2: Podocyte-specific deletion of PPARγ does not modify kidney structure and function.

(A) RT-PCR analysis of PPARγ mRNA expression in primary culture of podocytes from Pod-PPARγ WT and Pod-PPARγ lox mice (means of 7 mice per group, of two independent experiments). (B) Urinary albumin excretion rates (means of 20 mice per group, of four independent experiments) and (C) blood urea nitrogen concentration at day 10 after NTS injection in groups of mice as in A (means of 6 mice per group, of two independent experiments). ** $P<0.005$ vs. Pod-PPARγWT mice.

Figure 3:
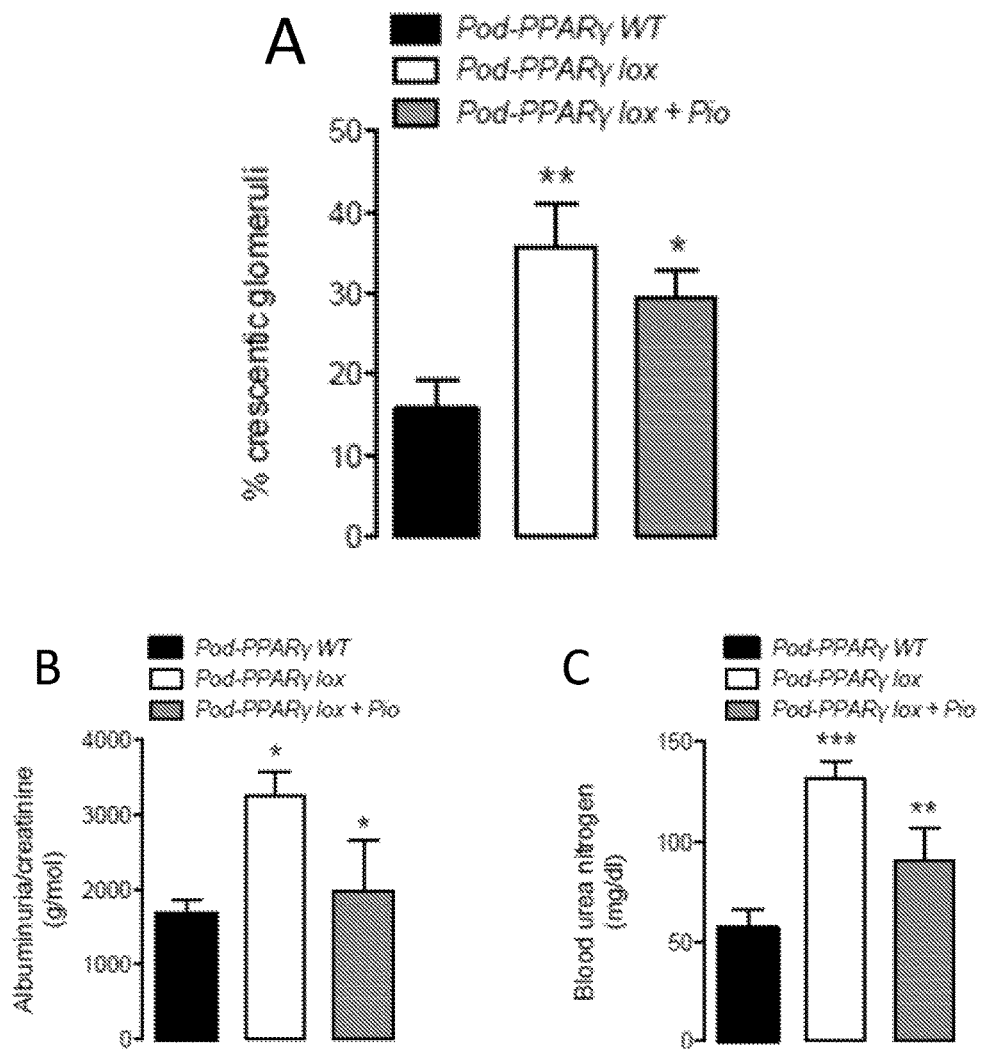

FIG. 3: Podocyte-specific deletion of Pparγ accelerates renal destruction in crescentic glomerulonephritis and limited effectiveness of pioglitazone administration in protecting from crescentic glomerulonephritis when the Pparγ gene is absent in podocytes.

(A) Proportion of crescentic glomeruli in kidneys from Pod-PPARγ WT and Pod-PPARγ lox mice with or without pioglitazone treatment at day 10 after NTS injection. (B and C) Albumin urinary excretion rate (B) and blood urea nitrogen concentration (C) at day 10 after NTS injection in groups of mice as in A. (Means of 17 mice per group, of three independent experiments). * $P<0.05$,  $P<0.01$, * $P<0.005$ vs. control mice.

Figure 4:
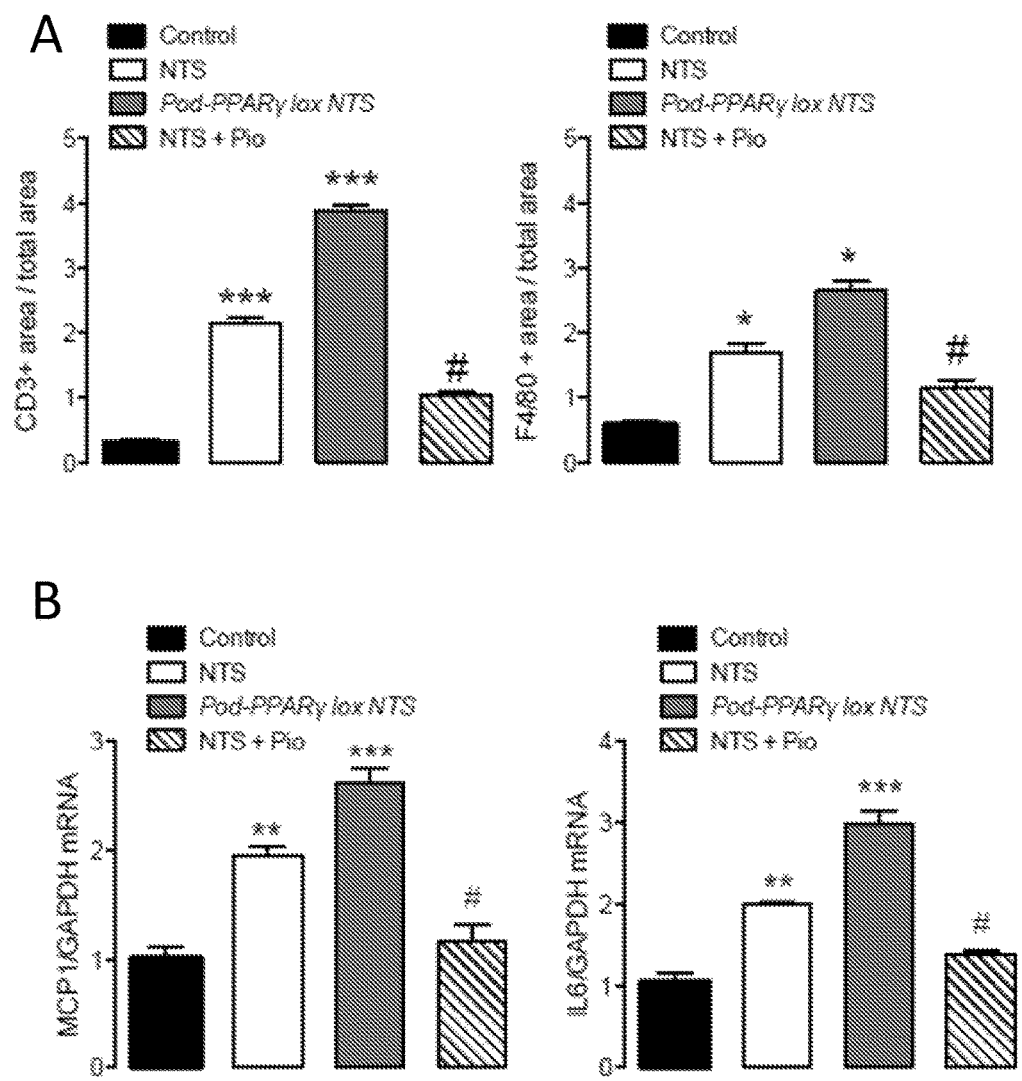

FIG. 4: Podocyte-specific deletion of PPARγ induces inflammatory cells infiltration in crescentic glomerulonephritis.

(A) quantification of CD3+ and F4/80+ infiltrates in renal cortex in controls and in NTS-injected wild-type with or without pioglitazone treatment or Pod-PPARγlox mice at day 10 after NTS injection (means of 8 mice per group, of two independent experiments). (B) mRNA expression of mcp1 and ll6 was determined by RT-PCR analysis in renal cortex tissue from groups of mice as in A (means of 8 mice per group, of two independent experiments). * $P<0.05$,  $P<0.01$, * $P<0.005$ vs. control mice and # vs. NTS-challenged mice (NTS).

Figure 5:
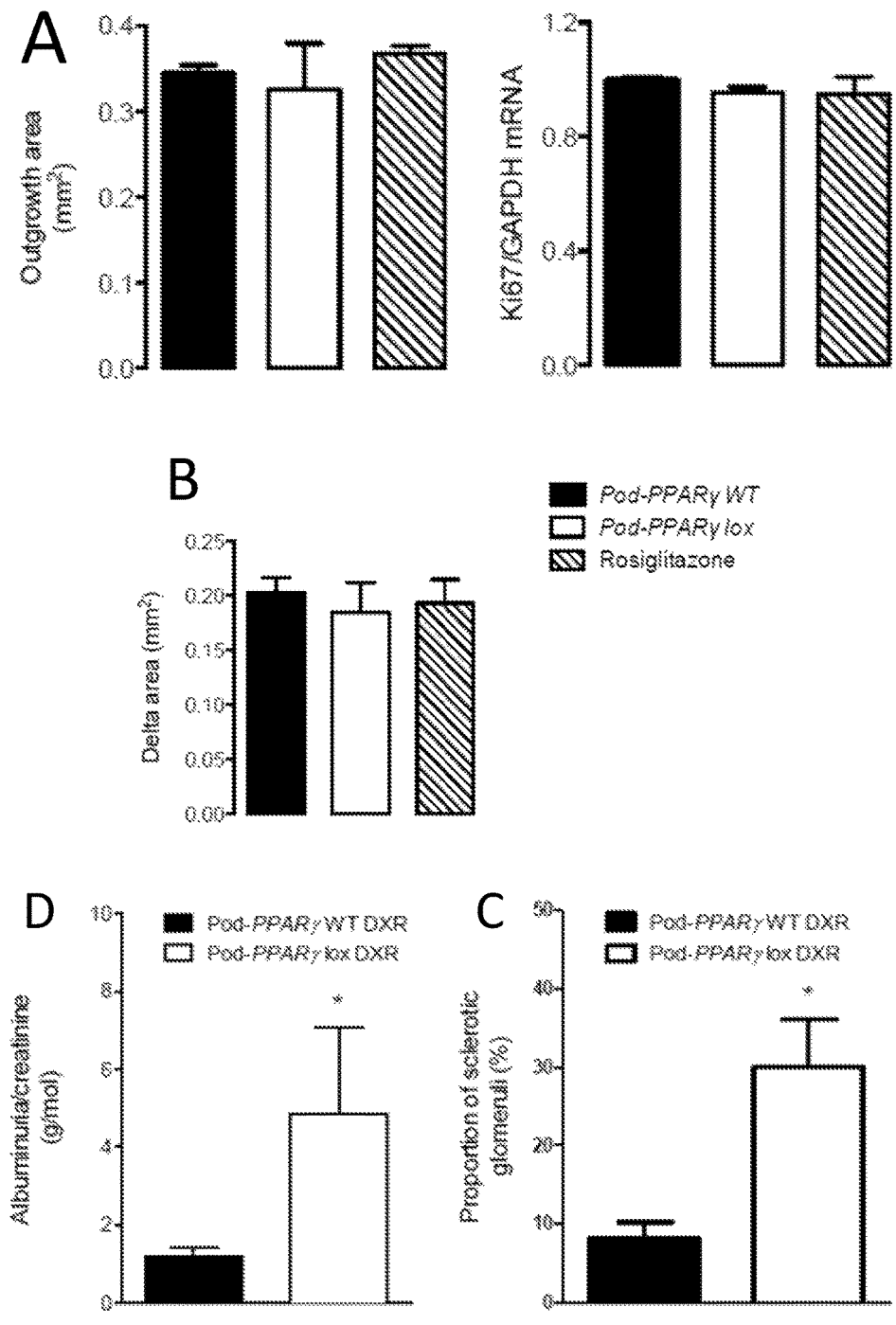

FIG. 5: Podocyte-specific deletion of Pparγ or rosiglitazone treatment does not modify proliferative and migratory podocyte in vitro.

Quantification of podocyte proliferation involving decapsulated glomeruli from Pod-PPARγ lox mice or podocytes treated with rosiglitazone (means of 11 mice per group, of three independent experiments). Podocyte outgrowth area was assessed after four days (A). Scale bars 20 μm. (A) RT-PCR analysis of the relative abundance of ki67 in primary podocyte cultures treated either with or without rosiglitazone (10 μM) for 16 hours, or from Pod-PPARγ lox mice (means of 5 mice per group, of two independent experiments). The migration of podocytes incubated either with or without rosiglitazone for 16 hours, or from Pod-PPARγ lox mice (means of 12 mice per group, of three independent experiments). Migration was assessed over a period of 12 hours (B). Scale bars 100 μm. Albumin urinary excretion rate (C), proportion of sclerotic glomeruli (D) at day 9 after doxorubicin administration in groups of Pod-PPARγ WT and Pod-PPARγ lox mice. (Means of 5 mice per group, of one experiment). * $P<0.05$ vs. control Pod-PPARγ WT mice.

(C) Representative photomicrographs of Masson trichrome-stained glomerular sections 9 days after doxorubicin administration to Pod-PPARγ WT and Pod-PPARγ lox mice.

Figure 6:
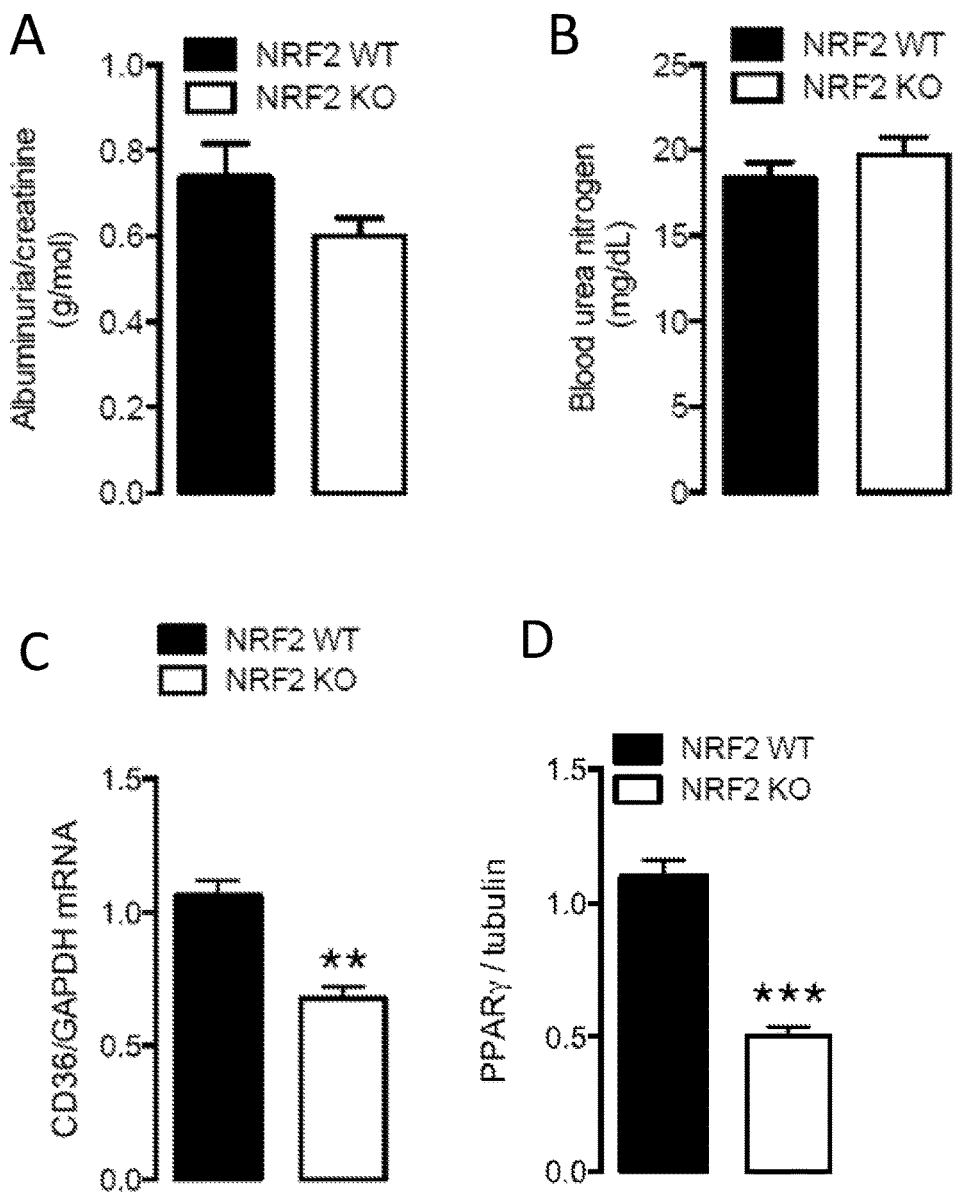

FIG. 6: Decrease in PPARγ activity in NRF2KO podocytes.

(A and B) Urinary albumin excretion rates (A) and blood urea nitrogen concentration (B) at baseline of NRF2KO and NRF2WT 10-week-old mice. (C) PPARγ activity determined by RT-PCR analysis of the relative abundance of cd36 in primary podocyte cultures from NRF2WT or NRF2KO mice. (D) PPARγ expression in primary podocyte cultures (D) and glomeruli from NRF2WT or NRF2KO mice. Values are means of 6 mice per group, of two independent experiments. * $P<0.05$,  $P<0.01$, * $P<0.001$ vs. NRF2WT mice.

Figure 7:
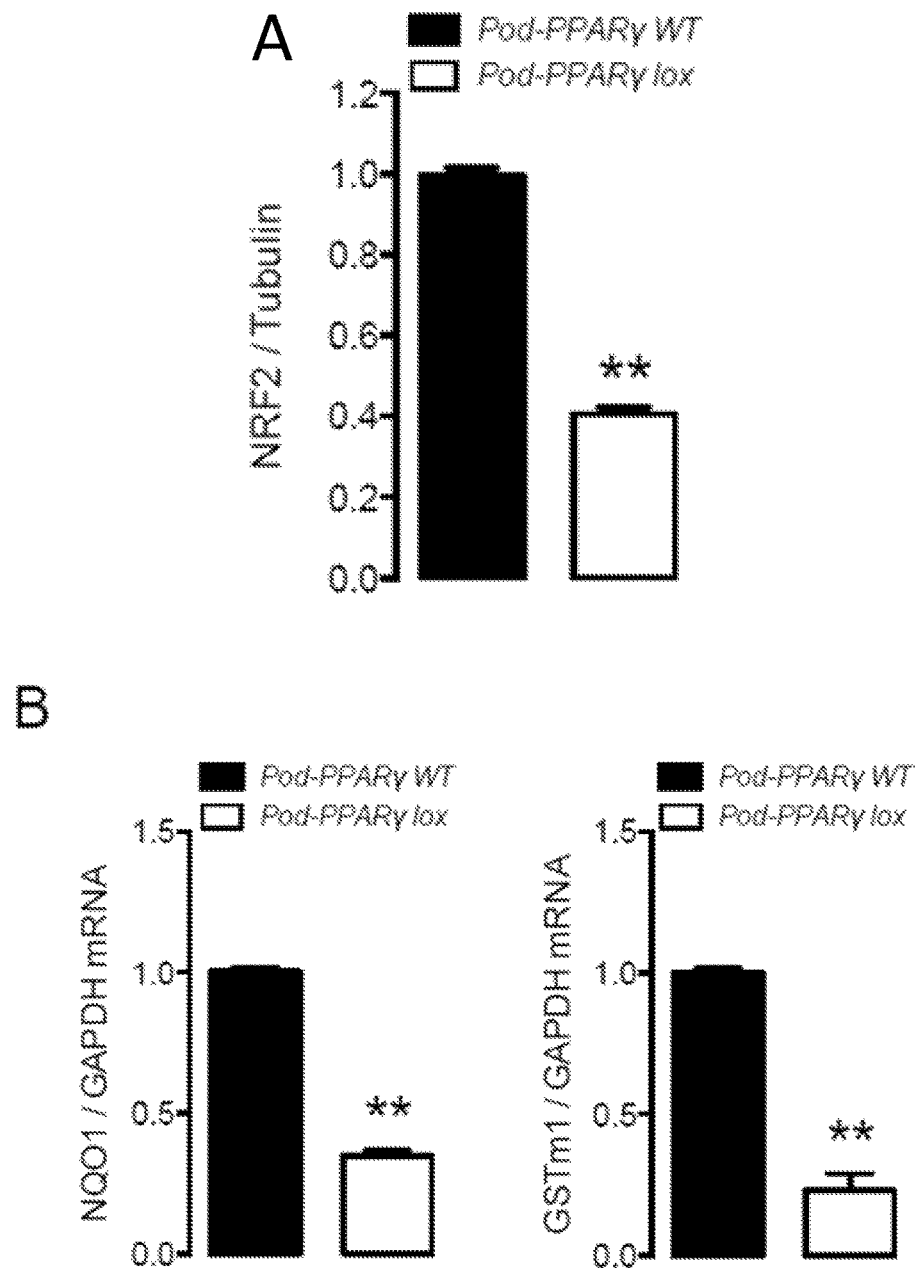

FIG. 7: Decrease in NRF2 pathway in podocyte-specific deletion of PPARγ mice.

(A) Western blots analysis of NRF2 in isolated glomeruli from Pod-PPARγ WT and Pod-PPARγ lox mice at baseline (means of 6 mice per group, of two independent experiments). (B) NRF2 activity determined by RT-PCR analysis of the relative abundance of Nqo1 and Gstm1, as NRF2 target genes, in primary podocyte cultures from Pod-PPARγ WT and Pod-PPARγ lox mice. Values are means±sem from 5 mice. ** $P<0.01$ vs. Pod-PPARγ WT mice.

Figure 8:
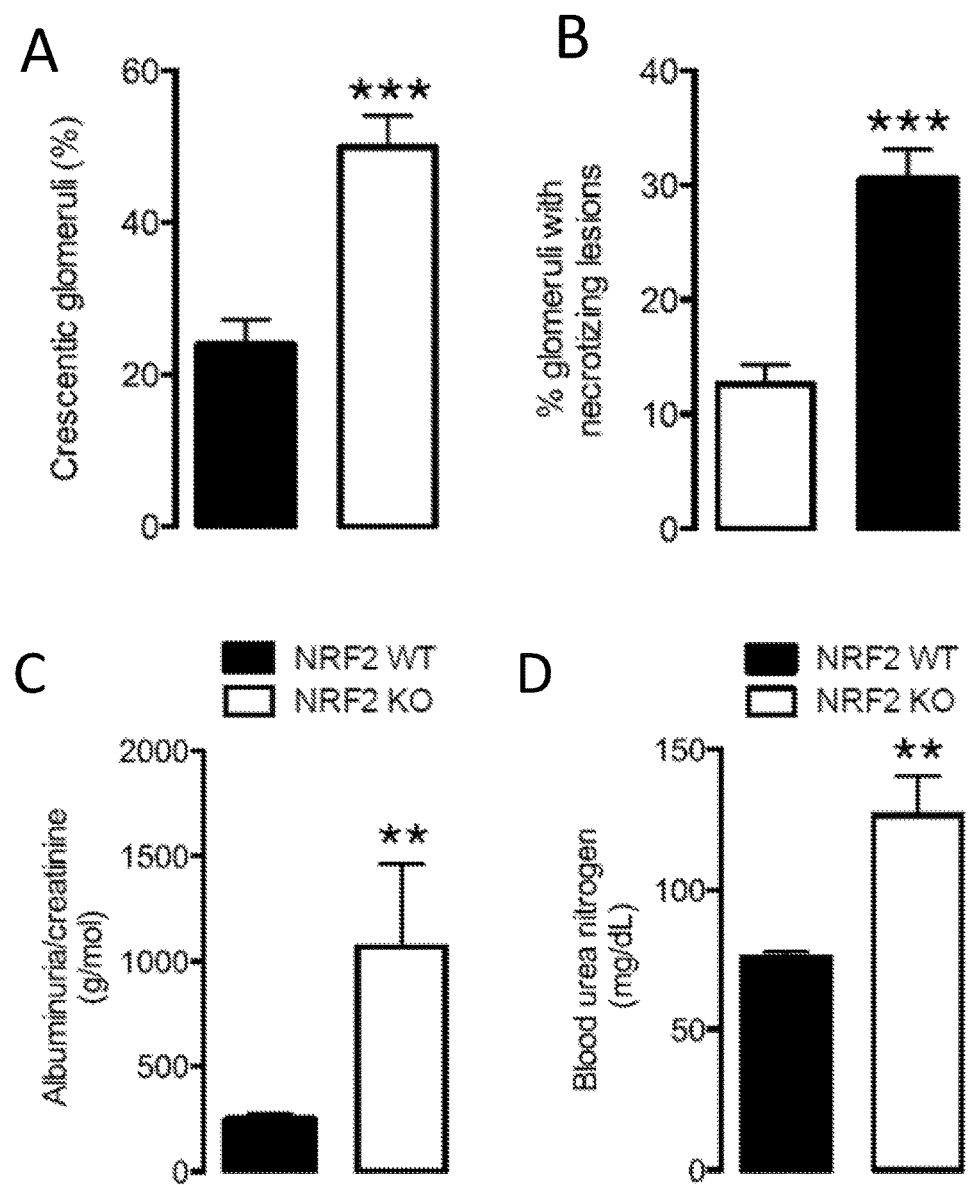

FIG. 8: NRF2 deficient mice develop more severe glomerulonephritis than normal littermates.

(A-B) Proportion of crescentic glomeruli (A) and glomeruli with necrotizing lesions (B) of NRF2KO and NRF2WT 10 days after NTS injection (means of 15 mice per group, of four independent experiments). Scale bars, 20 μm. (C)

Albuminuria and (D) blood urea nitrogen concentrations in NTS-challenged NRF2KO and NRF2WT mice (means of 15 mice per group, of four independent experiments). P<0.01, * P<0.001 vs. NTS-injected NRF2WT mice.

Figure 9:
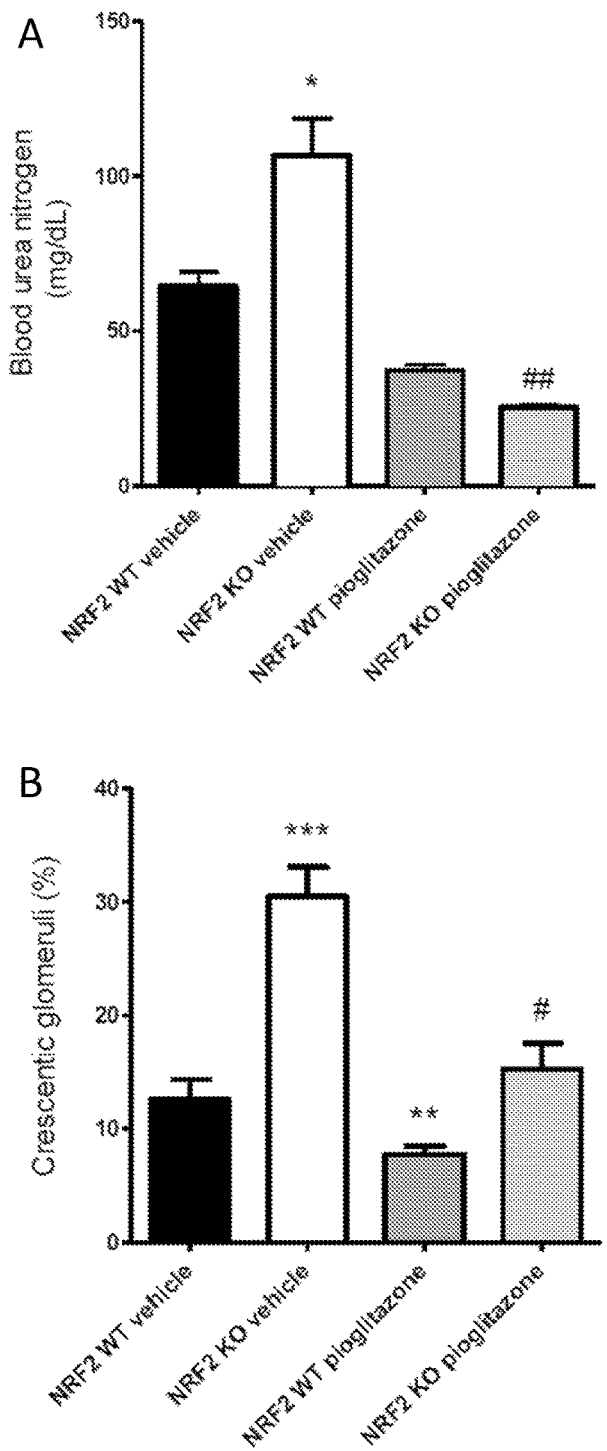

FIG. 9: PPARγ agonism attenuates the deleterious consequences of NRF2 deficiency in RPGN.

(A) blood urea nitrogen concentrations and proportion of crescentic glomeruli (B) in NTS-challenged NRF2KO and NRF2WT mice treated with pioglitazone or vehicle (means of 4-10 mice per group, one experiment). *P<0.05,  P<0.01, * P<0.001 vs. NTS- and vehicle-treated NRF2WT mice. ## P<0.01 vs. vehicle-treated NRF2KO nephritic group.

Figure 10:
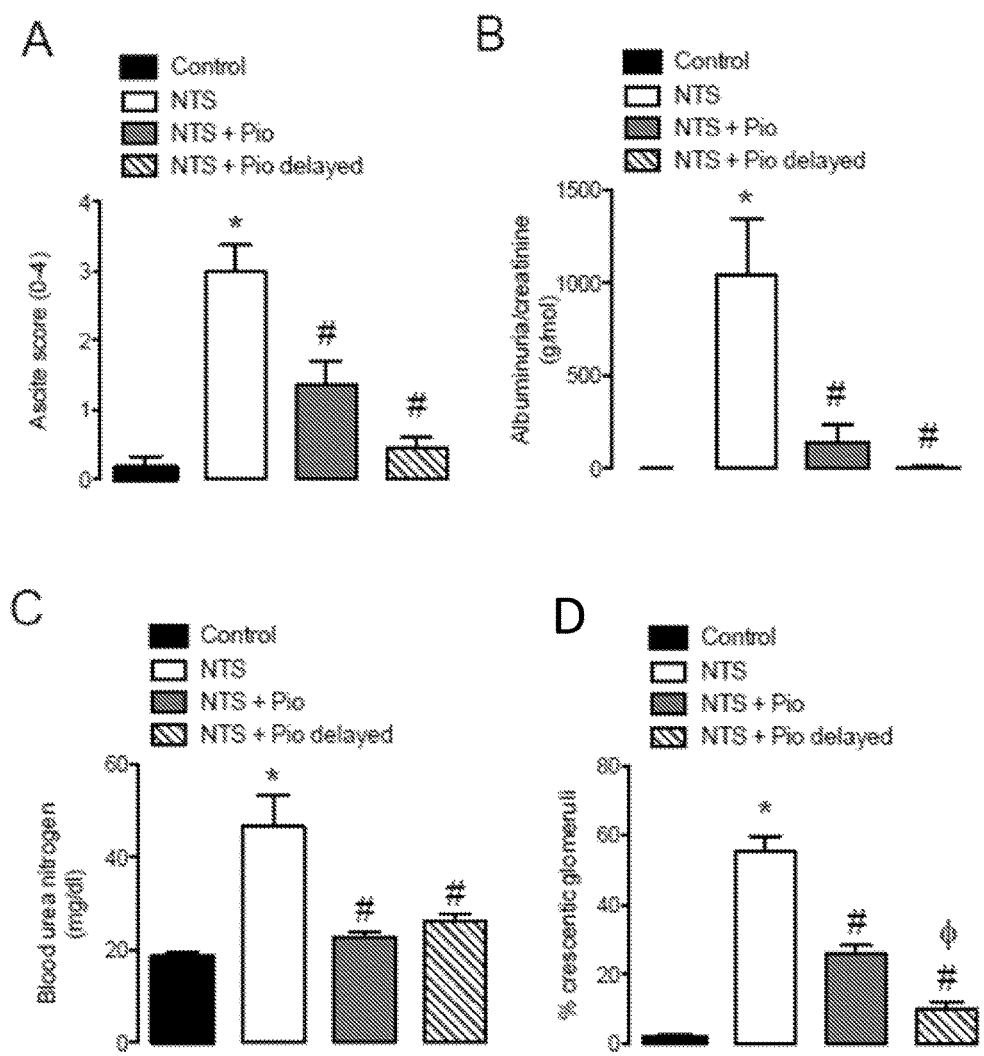

FIG. 10: Pioglitazone treatment improves glomerular structure and function in crescentic glomerulonephritis.

(A) Ascites score as index of albumin plasma loss and water and sodium retention. Ascites were quantified with a five-point scale (0-4) on the day mice were killed. (B) Urinary albumin excretion rates (C) and blood urea nitrogen concentration at day 10 after NTS injection in non-injected mice (control), NTSchallenged mice (NTS) or NTS-challenged mice treated with pioglitazone started in same time of NTS (NTS+Pio) or in a delayed manner (NTS+Pio delayed). (D) Proportion of crescentic glomeruli in groups of mice as in B. Values are means±sem of 8-12 mice per group, of two independent experiments. * P<0.05 vs. control mice, # P<0.05 vs. NTS-challenged mice (NTS), Φ P<0.05 vs. NTS+Pio.

EXAMPLE

Material & Methods

Animals

Podocyte-specific disruption of Ppary alleles were generated by crossing podocin-Cre positive mice (Moeller, Genesis, 2003) with the B6.129S6-Ppargtm1.1Mgn/Mmmh strain obtained from the Mutant Mouse Regional Resource Center at the University of Missouri (stock number 012035-MU) (herein named Ppary floxed mice) (Jones et al., 2002) on a C57BL6/J background. Their littermates with no deletion of Ppary alleles in any cells are considered as controls. Direct comparison was made between littermates age-matched controls.

Nrf2 mutant mice (Itoh et al., 1997) were maintained at our facility by breeding congenic Nrf2+/− mice. Age-matched congenic male Nrf2−/− and Nrf2+/+ (herein called Nrf2KO and Nrf2WT respectively) were compared.

Pharmacological activation of PPARγ was achieved with a thiazolidinedione (Pioglitazone), a synthetic ligands for PPARs inducing a modulation of target gene transcription. Pioglitazone (Takeda) was administered in oral gavage each day during 10 days (30 µg/bw g/day). Ten-week old C57B16/J male mice were randomly treated with pioglitazone and were compared to vehicle-treated (H20) littermates.

All experimental animal protocols were conducted were performed in accordance with guidelines of the European Community (L358-86/609EEC), and were approved by the Institut National de la Santé et de la Recherche Médicale and local Ethic Review Board at Paris Descartes University (Paris, France).

Induction of Crescentic Glomerulonephritis

The glomerulonephritis was induced on male mice (10-12 weeks of age) by intravenous injection of 15 µL of sheep anti-mouse glomerular basement membrane (GBM) nephrotoxic serum (NTS), which was diluted with 85 µL of sterile phosphate buffer solution. Serum injections were repeated twice (on days 2 and 3) as previously reported (Hochheiser et al., 2013; Huang et al., 2014).

Mouse Model for Doxorubicin-Induced Nephropathy

For the induction of doxorubicin (DXR) nephropathy, 12-week-old males were treated with single intravenous injection of DXR (15 mg/kg body weight diluted in 0.9% saline). Control mice received saline solution alone. All mice were weighed and urine samples were collected. Mice were sacrificed 16 days after DXR nephropathy induction.

Biochemical Measurements in Blood and Urine

Urinary creatinine and blood urea nitrogen (BUN) concentrations were analyzed by a standard colorimetric method (Olympus AU400) at the Biochemistry Laboratory of Institut Claude Bernard (IFR2, Faculté de Médecine Paris Diderot). Urinary albumin excretion was measured using a specific ELISA assay for quantitative determination of albumin in mouse urine (CellTrend GmbH).

Glomeruli Isolation and In Vitro Assays in Cultured Podocytes

Mouse kidneys were extracted, minced, and digested in 2 mg/mL collagenase I solution (Gibco) in RPMI 1640 (Invitrogen) at 37° C. for 3 minutes. Then filtered through a 70-µm cell strainer and one more through a 40-µm cell strainer. The homogenate was centrifuged at 720 g for 6 minutes and cells plated. Isolated glomeruli were then collected in Phosphosafe extraction buffer (Novagen) for protein extraction or in RLT extraction buffer (Qiagen) for total RNA extraction as previously reported (Bollee et al., 2011; Lenoir et al., 2014). For podocyte primary culture, freshly isolated glomeruli were plated in 6-plate dishes in RPMI 1640 (Invitrogen) supplemented by 10% Fetal Calf Serum (Biowest) and 1% penicillin-streptomycin (Invitrogen). The outgrowth of podocytes started between days 2 and 3. Podocyte outgrowth area was quantified at day 4 using ImageJ software (Bollee et al., 2011).

After 4 days of primary culture, podocytes were trypsinized then plated into µ-Dish 35 mm high with Culture-Insert (Ibidi). Ibidi wounding inserts were used for cell migration studies. The coverage of the 500-µm gap was assessed after 12 hours of culture and podocyte migration area was quantified using Image J software. The effect of rosiglitazone (10 µM) on differentiated podocytes was tested during 16 hours. After stimulation, podocytes were scrapped in Phosphosafe buffer for protein extraction or in RLT buffer for total RNA extraction.

Histology

Kidneys were harvested and fixed in 4% formal. Paraffin-embedded sections (5 µm thick) were stained by Masson's trichrome to evaluate kidney morphology and determine proportion of crescentic glomeruli by a blinded examination on at least 50 glomeruli per section.

Immunohistochemistry and Immunofluorescence

Deparaffinized kidney sections were incubated for 30 minutes at 95° C. in the target retrieval solution (S1699, Dako), then in peroxidase blocking reagent (S2001, Dako), blocked in PBS containing 5% BSA and immunostained against PPARγ (Abcam), Podocalyxin (R&D systems), CD3 (DAKO) or F4/80 (AbD serotec). For PPARγ, CD3, F4/80, specific staining was revealed using Histofine reagents (Nichirei Biosciences), which contained anti-rabbit or anti-rat immune-peroxidase polymer for mouse tissue sections. PPARγ primary antibody was followed by a secondary rabbit anti-goat IgG Cyanin3 and podocalyxin primary antibody was followed by a secondary donkey anti-goat IgG AF488-conjugated antibody (Invitrogen). Podocyte culture cells were immunostained against WT1 (Abcam) and NRF2

(Abcam). The nuclei were stained using DAPI. Images were obtained on an AxioImager Z1 microscope apoptome with AxioCam camera (Zeiss).

Transmission Electron Microscopy Procedure

Small pieces of renal cortex were fixed in 4% glutaraldehyde, postfixed in 1% osmium tetroxide and embedded in epoxy resin. Ultrathin sections were counterstained with uranyl acetate and examined in a JEOL 1011 transmission electron microscope with Digital Micrograph software for acquisition.

Western Blot Analysis

After extraction from glomeruli or podocytes with lysis buffer, proteins were quantified by BCA protein assay kit (iNtRON Biotechnology). Samples were resolved on 4-12% Bis-Tris Criterion XT gels (Bio-Rad) then transferred to a polyvinylidene difloride membrane. Membranes were incubated with the appropriate primary antibodies: rabbit anti-PPARγ (Abcam), rabbit anti-NRF2 (Abcam). Protein loading was monitored by using the rat antitubulin antibody (Abcam). Secondary antibodies were donkey-anti rabbit HRP (GE Healthcare Life Sciences). Antigens were revealed by enhanced chemiluminescence (Supersignal West Pico, Pierce) and detected on a LAS-4000 imaging system (Fuji). Densitometric analysis with Image J software was used for quantification.

Real-Time PCR

Total RNA extraction of mice glomeruli was performed using an Rneasy Minikit (Qiagen) and reverse transcribed into cDNA using the Quantitect Reverse Transcription kit (Qiagen) according to the manufacturer's protocol. cDNA and standard were amplified in Maxima SYBR Green/Rox qPCR mix (Fermentas) on an ABI PRISM thermo cycler. The comparative method of relative quantification (2-ΔΔCT) was used to calculate the expression level of each target gene, normalized to GAPDH. The oligonucleotide sequences are available upon request. The data are presented as the fold change in gene expression.

Statistical Analyses

All values are expressed as means+SEM. Statistical analyses were calculated using GraphPad Prism software (La Jolla, Calif.). Comparison between two groups was performed by using Mann-Whitney t test. Comparison between multiple groups was performed by using one-way ANOVA followed by Tukey post test. Values of $P<0.05$ were considered significant.

Results

Glomerular PPARγ Expression is Decreased in Experimental RPGN

We sought to determine if PPARγ expression could be altered in glomeruli during RPGN. Immunoblot analysis showed a 65% decrease in PPARγ glomerular expression in nephritic mice at day 10 compared to baseline (FIG. 1 A). CD36 mRNA expression was consistently reduced in glomerular extracts from NTS-challenged mice compared to control, suggesting blunted PPARγ transcriptional activity in RPGN (FIG. 1 B). Interestingly, the loss of most glomerular PPARγ immunofluorescence in nephritic glomeruli was found in podocytes.

Podocyte-Specific Deletion of PPARγ does not Modify Kidney Structure and Function To determine the role of the podocyte PPARγ pathway during experimental RPGN, we generated mice with a podocyte-specific deletion of Pparγ by using the NPHS2-Cre recombinase or podocin-Cre mouse (Pod-Cre), which expresses Cre-recombinase exclusively in podocytes starting from the capillary loop stage during glomerular development (Moeller et al., 2003). Confirmation of the deletion was assessed by RTPCR which showed a significant reduction in Pparγ mRNA level in isolated podocytes of podocin-Cre Pparγ lox/lox (Pod-PPARγ lox) mice compared to control animals (Pod-PPARγ WT) (FIG. 2 A). The purity of the primary podocyte culture was validated by nephrin and podocin immunostaining as previously described (Lenoir et al., 2014). Similarly, double immunofluorescence staining revealed a marked decrease in PPARγ expression in glomeruli from Pod-PPARγ lox mice. Adult Pod-Pparγ lox mice showed no abnormalities in glomerular morphology, urinary albumin excretion and renal function as estimated by BUN levels (FIGS. 2 B-2 C).

Podocyte-Specific Deletion of PPARγ Accelerates Renal Destruction in Experimental RPGN.

The inventors challenged Pod-Pparγ lox mice and littermate controls with NTS to study the in vivo contribution of PPARγ in podocytes to the development of inflammatory glomerular injury. At day 10 after NTS injection, Pod-Pparγ lox mice exhibited more severe glomerulonephritis with crescent formation increased by 2 to 3 fold compared to controls (FIG. 3 A). Nevertheless, the anti-GBM humoral response remained unchanged. The specific deletion of PPARγ within podocytes induced ultrastructural changes with the loss of an interdigitating foot process pattern. This was associated with aggravated renal dysfunction reflected by significantly increased proteinuria and BUN in Pod-Pparγ lox mice compared to controls (FIGS. 3 B & 3 C). To determine the extent to which pioglitazone prevented glomerular damage through stimulation of PPARγ on podocytes we treated nephritic Pod-Pparγ lox mice with either vehicle or pioglitazone. There was no difference in phenotype between the two groups suggesting that pioglitazone administration has limited efficacy in protecting from RPGN in the absence of a functional PPARγ system in podocytes (FIG. 3 A).

Effects of Systemic or Podocyte PPARγ Pathway Inhibition on Kidney Inflammation.

NTS-challenged mice exhibited an accumulation of inflammatory cells (F4/80 and CD3 positive) in the renal interstitium and around glomeruli. There was also an upregulation of monocyte chemoattractant protein 1 (Mc1) and interleukin-6 (IL6) mRNA in the glomeruli of these mice. Pioglitazone treatment significantly reduced both the number of infiltrating F4/80 and CD3 positive cells around glomeruli (FIG. 4 A) as well as MCP1 and IL6 mRNA expression (FIG. 4 B). Surprisingly, podocyte-specific deletion of PPARγ alone induced a significant increase in infiltrating cells and MCP1 and IL6 mRNA in the renal cortex during RPGN (FIGS. 4 A and 4 B) suggesting a potent local anti-inflammatory role for podocyte PPARγ.

Podocyte-Specific Deletion of PPARγ or Rosiglitazone Treatment does not Modify Proliferative and Migratory Podocyte In Vitro.

To determine the role of the podocyte PPARγ we performed primary cultures of podocytes to assess their proliferation and migration, both hallmarks of podocyte dedifferentiation and crescent formation. In many cell types, it has been showed that PPARγ controls cell proliferation and apoptosis (Goke et al., 2000; Martelli et al., 2002; Sato et al., 2000). PPARγ activators may also inhibit cell migration and invasion (Marx et al., 1998; Motomura et al., 2004; Sato et al., 2000). Podocyte outgrowth area and Ki67 mRNA expression were no different in glomeruli isolated from Pod-PPARγ lox mice, those taken from Pod-PPARγ WT mice and those from Pod-PPARγ WT and treated with rosiglitazone in vitro (FIG. 5 A). Moreover, neither PPARγ activation nor podocyte-specific deletion of PPARγ had any effect on podocyte motility (FIG. 5 B).

Podocyte-Specific PparγDeletion Mice are More Susceptible to Doxorubicin Nephropathy.

Since PPARγ does not modulate podocyte proliferation or migration, we hypothesized that this pathway may prevent podocyte death. To this end, we challenged Pod-PPARγ lox and Pod-PPARγ wt mice with a second model of nephropathy involving direct podocyte toxicity and death. Doxorubicin (DXR) or adriamycin-induced nephropathy is an experimental analog of human focal segmental glomerulosclerosis, which presents as severe podocyte injury and proteinuria, followed by recruitment of parietal epithelial cells and scarring of the glomerulus (Lee and Harris, 2011). We were unable to detect a significant difference in a basal level of protein in the urine between Pod-PPARγ lox and Pod-PPARγ wt mice; however, the DXR-induced proteinuria was significantly exacerbated in the Pod-PPARγ lox mice (FIG. 5 C). Likewise, Pod-PPARγ lox displayed more glomerular podocyte-parietal epithelial cell bridges and focal segmental sclerosis than their wilt-type counterparts (FIG. 5 D).

Decrease in PPARγActivity in Nuclear Factor Erythroid 2-Related Factor 2 (NRF2) Deficient Podocytes and Decrease in NRF2 Pathway in PPARγ Deficient Podocytes.

We then searched for candidates for the metabolic regulation of PPARγ abundance in podocytes. The nuclear factor erythroid 2-related factor 2 (NRF2), a redox-sensitive member of the cap "n" collar basic leucine zipper family, plays a vital role in cytoprotection against oxidative and electrophilic stress as well as in suppression of inflammation (Osburn and Kensler, 2008). Recently, microarray analysis of NRF2 target genes demonstrated that PPARγ expression is compromised in Nrf2-/- (NRF2KO) mice (Cho et al., 2010; Cho et al., 2005; Huang et al., 2010). This could be a direct effect of the lack of NRF2 since NRF2 induces PPARγ binding to at least two ARE sequences in the upstream promoter region (Cho et al., 2010; Huang et al., 2010). Thus, we assessed PPARγ expression and activity in glomeruli and podocytes from NRF2KO mice. First, NRF2KO mice displayed no abnormalities in kidney structure and function. Glomerular structure by light and electron microscopy were conserved in NRF2KO mice ultrastructure. Similarly, albumin to creatinine ratio and BUN concentrations were similar to wild-type mice (FIGS. 6 A and 6 B). CD36 mRNA (FIG. 6 C) and PPARγ protein (FIG. 6 D) expression were reduced in glomerular extracts from NRF2KO mice, suggesting reduced PPARγ transcriptional activity as compared to NRF2WT glomeruli. Moreover, immunoreactive PPARγ was reduced in kidney sections from NRF2KO mice compared to controls.

To analyze the crosstalk between NRF2 and PPARγ, we also investigated NFR2 abundance and activity in podocytes upon genetic manipulation of PPARγ level. Compared to Pod-Pparγ WT mice, isolated glomeruli from Pod-Pparγ lox mice showed reduced NRF2 expression and activity as reflected by NAD(P)H quinone oxidoreductase 1 (Nqo1) and glutathione S-transferase (Gstm1) mRNA levels or (FIGS. 7 A and 7 B). In addition, Pparγ gene deletion decreased NRF2 nuclear translocation, as shown by decreased NRF2 fluorescence and nuclear accumulation. Overall, these data suggest that the PPARγ pathway is altered in glomeruli from NRF2KO mice and vice versa.

NRF2 Deficiency Aggravates RPGN in Mice in a PPARγ-Dependent Fashion.

As we found the Nrf2 and PPARγ pathways to be linked in podocytes and as both are known to modulate oxidative stress responses, we went on to evaluate whether NRF2 deficient mice would demonstrate a similar kidney phenotype to Pod-PPARγ lox mice in experimental RPGN.

As expected, NRF2WT mice exhibited crescent formation and renal dysfunction. Interestingly, NRF2KO mice developed more aggressive glomerulonephritis compared to controls as shown by a 2-fold higher incidence of crescent formation (FIG. 8 A), and three times as many glomeruli with necrotizing lesions (FIG. 8 B). These histological differences were associated with more severe functional renal impairment in NRF2KO than in NRF2WT animals (FIGS. 8 C & 8 D). Ultrastructural analysis of kidney from the NRF2KO mice showed extensive podocyte foot process fusion and glomerular basement membrane thickening. These data suggest that NRF2 deficiency markedly aggravates experimental RPGN and that NRF2KO mice have a similar renal phenotype to Pod-PPARγ lox mice in experimental RPGN.

To decipher to which extent the increased severity of RPGN caused by NRF2 deficiency could be linked to altered PPARγ activity, we administered pioglitazone to NRF2KO mice and wild type congenic littermates in experimental RPGN. Pioglitazone administration alleviated albumin urinary excretion by three-fold, renal failure as assessed by BUN levels (FIG. 9 A) and likewise, glomerular damage (FIG. 9 B).

PPARγ Gain of Function Approach with Pioglitazone Treatment Improves Glomerular Structure and Function in Experimental RPGN In the model of RPGN, crescent formation was associated with significantly reduced PPARγ expression and activity in glomeruli, especially in podocytes. As these observations suggested that alterations in PPARγ may be involved in crescent formation, albuminuria and renal failure we went on to test whether pharmacological stimulation of the PPARγ pathway prevented or treated renal damage. To determine whether stimulation of the PPARγ pathway could be a therapeutic option for RPGN, we administered a clinically available TZD, pioglitazone, on day 4 after infusion of anti-GBM NTS. This time point was chosen as it is clinically relevant, associated with peaks in both albuminuria and serum creatinine. This regimen was compared to the effects of vehicle alone and to the administration of pioglitazone 6 hours prior to first infusion of NTS.

Ten days after RPGN induction, mice developed significant ascites, hypoalbuminemia and albuminuria characteristic of the nephrotic syndrome. Pioglitazone administration, given prior to and following NTS, was associated with a lower incidence and severity of ascites and less albuminuria than in vehicle-treated (NTS) mice (FIGS. 10 A & 10 B). Furthermore, whereas vehicle only-treated mice (NTS) developed rapid and lifethreatening renal failure, mice treated with pioglitazone, before and after NTS, -had BUN levels within the normal range (FIG. 10 C). The functional protection conferred by pioglitazone administration was associated with marked alleviation of histopathological damage as measured in Masson-trichrome stained cortex sections (FIG. 10 D).

Discussion

In the present study, we have demonstrated that in NTS-induced RPGN, mice with a podocyte-specific deletion of Pparγ are much more prone to crescentic damage, podocyte loss and renal failure than their wild-type counterparts. These results suggest PPARγ signaling activation in podocytes limits susceptibility to develop RPGN. These novel data shed light on the pathophysiological actions of the PPARγ system in RPGN and represent the first example of specific involvement of the glomerular PPARγ system in the pathophysiology of a form of severe extracapillary glomerulonephritis. Mirroring the loss of function approach, a gain of function approach allowed very significant histopathological and functional protection of glomeruli despite untouched anti-GBM humoral response. Moreover, delayed onset administration ("therapeutic scheme") of the TZD was as effective as the prevention scheme. More than ten years ago, pioneering preventive administration of troglitazone or pioglitazone in WKY rats was shown to alleviate urinary protein excretion and crescent formation after experimental anti-GBM disease (Haraguchi et al., 2003). Although, evidence has since accumulated that PPARγ influences podocyte survival in vitro and in vivo, PPARγ activity was also expected to exert anti-angiogenic effects (Panigrahy et al., 2002; Scoditti et al., 2010), a potentially major detrimental effect in the context of RPGN which is accompanied by marked endothelial injury. Thus, no further investigation of this major pathway has been conducted in this form of extracapillary glomerulonephritis. The authors had noticed blunted kidney infiltration of ED-1-positive monocyte/macrophages and CD8-positive cells into glomeruli and attributed the beneficial disease-modifying effects of TZD administration to the recruitment of inflammatory cells via a PPARγ-dependent mechanism (Haraguchi et al., 2003).

In fact, our data lead to re-interpretation of the paradigm that PPARγ agonism would primarily influence the course of disease through anti-inflammatory actions such as described in endothelial cells, monocytes-macrophages and dendritic cells (Bouhlel et al., 2007; Chinetti et al., 1998; Straus and Glass, 2007). Podocyte-specific abrogation of PPARγ exacerbated RPGN-related renal injury illustrating the crucial homeostatic local role for this transcription factor. In this model, the humoral and the cellular immune responses were not targeted. Notably, PPARγ deficiency did not directly influence podocyte proliferation and migration as observed in primary cultures of podocytes in vitro but significantly attenuated peri-glomerular infiltrates of T cells and macrophages as well as MCP1 and IL6 mRNA abundance in the cortex of nephritic mice. Therefore, we cannot exclude PPARγ-dependent paracrine effects of the diseased podocytes on surrounding inflammatory cells such as limitation of endogenous danger signals released by injured cells. The DXR model of FSGS was also used. Evidence from animal models and in-vitro studies suggests that injury inherent within or directed to the podocyte is a central pathogenetic factor to FSGS (D'Agati, 2012). Again, PPARγ gene deletion in podocytes only was sufficient to significantly accentuate podocyte loss, albuminuria and sclerosis. These data suggest that PPARγ may critically sustain podocyte survival and function upon inflammatory (RPGN) or toxic (FSGS) injury.

To address the relative role of TZD administration in multiple kidney and immune compartments in response to NTS challenge, we treated animals with podocyte selective PPARγ-deficiency with a regimen that was effective in wild type animals. Surprisingly, TZD administration did not efficiently alleviate RPGN in Pod-PPARγ lox mice, suggesting that a significant part of the beneficial action of pioglitazone administration is mediated through the podocyte PPARγ pathway. These findings unveil the pivotal role of homeostatic systems in glomerular resident cells to cope with inflammatory stress.

Another salient feature of our study is that crosstalk between the NRF2 and PPARγ pathways was observed in primary podocytes in vitro and in vivo. Whereas NRF2 induces PPARγ binding to at least two ARE sequences in the upstream promoter region (Cho et al., 2010; Huang et al., 2010), the mechanism whereby PPARγ activity modulates NRF2 transcriptional activity remains elusive. In the context of severe immune-complex mediated podocyte injury, a significant Nrf2-driven PPARγ induction has an essential protective role in glomerular oxidant injury as TZD administration could overcome part of the deleterious effect of NRF2 complete deficiency.

In summary, our study demonstrates the pivotal role of the local PPARγ system in maintaining podocyte quiescence and orchestrating the global glomerular tolerance to a severe immune-complex-mediated disease. PPARγ was found to be a downstream effector of the NRF2 pathway, unveiling the critical protective role of both NRF2 activity and PPARγ. We also provide proof of principle that delayed PPARγ agonism could display therapeutic action on glomerular function and structure in a severe model of RPGN.

REFERENCES

Throughout this application, various references describe the state of the art to which this invention pertains. The disclosures of these references are hereby incorporated by reference into the present disclosure.

Ahmadian, M., J. M. Suh, N. Hah, C. Liddle, A. R. Atkins, M. Downes, and R. M. Evans. 2013. PPARgamma signaling and metabolism: the good, the bad and the future. *Nat Med* 19:557-566.

Bariety, J., C. Mandet, G. S. Hill, and P. Bruneval. 2006. Parietal podocytes in normal human glomeruli. *J Am Soc Nephrol* 17:2770-2780.

Besse-Eschmann, V., M. Le Hir, N. Endlich, and K. Endlich. 2004. Alteration of podocytes in a murine model of crescentic glomerulonephritis. *Histochem Cell Biol* 122:139-149.

Bollee, G., M. Flamant, S. Schordan, C. Fligny, E. Rumpel, M. Milon, E. Schordan, N. Sabaa, S. Vandermeersch, A. Galaup, A. Rodenas, I. Casal, S. W. Sunnarborg, D. J. Salant, J. B. Kopp, D. W. Threadgill, S. E. Quaggin, J. C. Dussaule, S. Germain, L. Mesnard, K. Endlich, C. Boucheix, X. Belenfant, P. Callard, N. Endlich, and P. L. Tharaux. 2011. Epidermal growth factor receptor promotes glomerular injury and renal failure in rapidly progressive crescentic glomerulonephritis. *Nat Med* 17:1242-1250.

Bouhlel, M. A., B. Derudas, E. Rigamonti, R. Dievart, J. Brozek, S. Haulon, C. Zawadzki, B. Jude, G. Torpier, N. Marx, B. Staels, and G. Chinetti-Gbaguidi. 2007. PPARgamma activation primes human monocytes into alternative M2 macrophages with anti-inflammatory properties. *Cell Metab* 6:137-143.

Buckingham, R. E., K. A. Al-Barazanji, C. D. Toseland, M. Slaughter, S. C. Connor, A. West, B. Bond, N. C. Turner, and J. C. Clapham. 1998. Peroxisome proliferatoractivated receptor-gamma agonist, rosiglitazone, protects against nephropathy and pancreatic islet abnormalities in Zucker fatty rats. *Diabetes* 47:1326-1334.

Calkin, A. C., S. Giunti, K. A. Jandeleit-Dahm, T. J. Allen, M. E. Cooper, and M. C. Thomas. 2006. PPAR-alpha and -gamma agonists attenuate diabetic kidney disease in the apolipoprotein E knockout mouse. *Nephrol Dial Transplant* 21:2399-2405.

Cha, D. R., X. Zhang, Y. Zhang, J. Wu, D. Su, J. Y. Han, X. Fang, B. Yu, M. D. Breyer, and Y. Guan. 2007. Peroxisome proliferator activated receptor alpha/gamma dual agonist tesaglitazar attenuates diabetic nephropathy in db/db mice. *Diabetes* 56:2036-2045.

Chinetti, G., S. Griglio, M. Antonucci, I. P. Torra, P. Delerive, Z. Majd, J. C. Fruchart, J. Chapman, J. Najib, and B. Staels. 1998. Activation of proliferator-activated receptors alpha and gamma induces apoptosis of human monocyte-derived macrophages. *J Biol Chem* 273:25573-25580.

Cho, H. Y., W. Gladwell, X. Wang, B. Chorley, D. Bell, S. P. Reddy, and S. R. Kleeberger. 2010. Nrf2-regulated PPAR{gamma} expression is critical to protection against acute lung injury in mice. *Am J Respir Crit Care Med* 182:170-182.

Cho, H. Y., S. P. Reddy, A. Debiase, M. Yamamoto, and S. R. Kleeberger. 2005. Gene expression profiling of NRF2-mediated protection against oxidative injury. *Free Radic Biol Med* 38:325-343.

D'Agati, V. D. 2012. Pathobiology of focal segmental glomerulosclerosis: new developments. *Curr Opin Nephrol Hypertens* 21:243-250.

Goke, R., A. Goke, B. Goke, and Y. Chen. 2000. Regulation of TRAIL-induced apoptosis by transcription factors. *Cell Immunol* 201:77-82.

Haraguchi, K., H. Shimura, and T. Onaya. 2003. Suppression of experimental crescentic glomerulonephritis by peroxisome proliferator-activated receptor (PPAR) gamma activators. *Clin Exp Nephrol* 7:27-32.

Heikkinen, S., J. Auwerx, and C. A. Argmann. 2007. PPAR-gamma in human and mouse physiology. *Biochim Biophys Acta* 1771:999-1013.

Henique, C., C. Papista, L. Guyonnet, O. Lenoir, and P. L. Tharaux. 2014. Update on crescentic glomerulonephritis. *Semin Immunopathol* 36:479-490.

Hochheiser, K., C. Heuser, T. A. Krause, S. Teteris, A. Ilias, C. Weisheit, F. Hoss, A. P. Tittel, P. A. Knolle, U. Panzer, D. R. Engel, P. L. Tharaux, and C. Kurts. 2013. Exclusive CX3CR1 dependence of kidney DCs impacts glomerulonephritis progression. *J Clin Invest* 123:4242-4254.

Huang, J., A. Filipe, C. Rahuel, P. Bonnin, L. Mesnard, C. Guerin, Y. Wang, C. Le Van Kim, Y. Colin, and P. L. Tharaux. 2014. Lutheran/basal cell adhesion molecule accelerates progression of crescentic glomerulonephritis in mice. *Kidney Int* Huang, J., I. Tabbi-Anneni, V. Gunda, and L. Wang. 2010. Transcription factor Nrf2 regulates SHP and lipogenic gene expression in hepatic lipid metabolism. *Am J Physiol Gastrointest Liver Physiol* 299:G1211-1221.

Itoh, K., T. Chiba, S. Takahashi, T. Ishii, K. Igarashi, Y. Katoh, T. Oyake, N. Hayashi, K. Satoh, I. Hatayama, M. Yamamoto, and Y. Nabeshima. 1997. An Nrf2/small Maf heterodimer mediates the induction of phase II detoxifying enzyme genes through antioxidant response elements. *Biochem Biophys Res Commun* 236:313-322.

Jones, J. R., K. D. Shelton, Y. Guan, M. D. Breyer, and M. A. Magnuson. 2002. Generation and functional confirmation of a conditional null PPARgamma allele in mice. *Genesis* 32:134-137.

Kanjanabuch, T., L. J. Ma, J. Chen, A. Pozzi, Y. Guan, P. Mundel, and A. B. Fogo. 2007. PPAR-gamma agonist protects podocytes from injury. *Kidney Int* 71:1232-1239.

Le Hir, M., C. Keller, V. Eschmann, B. Hahnel, H. Hosser, and W. Kriz. 2001. Podocyte bridges between the tuft and Bowman's capsule: an early event in experimental crescentic glomerulonephritis. *J Am Soc Nephrol* 12:2060-2071.

Lee, V. W., and D. C. Harris. 2011. Adriamycin nephropathy: a model of focal segmental glomerulosclerosis. *Nephrology (Carlton)* 16:30-38.

Lenoir, O., M. Milon, A. Virsolvy, C. Henique, A. Schmitt, J. M. Masse, Y. Kotelevtsev, M. Yanagisawa, D. J. Webb, S. Richard, and P. L. Tharaux. 2014. Direct action of endothelin-1 on podocytes promotes diabetic glomerulosclerosis. *J Am Soc Nephrol* 25:1050-1062.

Liu, H. F., L. Q. Guo, Y. Y. Huang, K. Chen, J. L. Tao, S. M. Li, and X. W. Chen. 2010. Thiazolidinedione attenuate proteinuria and glomerulosclerosis in Adriamycin-induced nephropathy rats via slit diaphragm protection. *Nephrology (Carlton)* 15:75-83.

Ma, L. J., C. Marcantoni, M. F. Linton, S. Fazio, and A. B. Fogo. 2001. Peroxisome proliferator-activated receptor-gamma agonist troglitazone protects against nondiabetic glomerulosclerosis in rats. *Kidney Int* 59:1899-1910.

Martelli, M. L., R. Iuliano, I. Le Pera, I. Sama, C. Monaco, S. Cammarota, T. Kroll, L. Chiariotti, M. Santoro, and A. Fusco. 2002. Inhibitory effects of peroxisome poliferator-activated receptor gamma on thyroid carcinoma cell growth. *J Clin Endocrinol Metab* 87:4728-4735.

Marx, N., U. Schonbeck, M. A. Lazar, P. Libby, and J. Plutzky. 1998. Peroxisome proliferator-activated receptor gamma activators inhibit gene expression and migration in human vascular smooth muscle cells. *Circ Res* 83:1097-1103.

Moeller, M. J., S. K. Sanden, A. Soofi, R. C. Wiggins, and L. B. Holzman. 2003. Odocytespecific expression of cre recombinase in transgenic mice. *Genesis* 35:39-42.

Moeller, M. J., A. Soofi, I. Hartmann, M. Le Hir, R. Wiggins, W. Kriz, and L. B. Holzman. 2004. Podocytes populate cellular crescents in a murine model of inflammatory glomerulonephritis. *J Am Soc Nephrol* 15:61-67.

Motomura, W., M. Nagamine, S. Tanno, M. Sawamukai, N. Takahashi, Y. Kohgo, and T. Okumura. 2004. Inhibition of cell invasion and morphological change by troglitazone in human pancreatic cancer cells. *J Gastroenterol* 39:461-468.

Nakamura, T., C. Ushiyama, S. Osada, M. Hara, N. Shimada, and H. Koide. 2001. Pioglitazone reduces urinary podocyte excretion in type 2 diabetes patients with microalbuminuria. *Metabolism* 50:1193-1196.

Osburn, W. O., and T. W. Kensler. 2008. Nrf2 signaling: an adaptive response pathway for protection against environmental toxic insults. *Mutat Res* 659:31-39.

Panigrahy, D., S. Singer, L. Q. Shen, C. E. Butterfield, D. A. Freedman, E. J. Chen, M. A. Moses, S. Kilroy, S. Duensing, C. Fletcher, J. A. Fletcher, L. Hlatky, P. Hahnfeldt, J. Folkman, and A. Kaipainen. 2002. PPARgamma ligands inhibit primary tumor growth and metastasis by inhibiting angiogenesis. *J Clin Invest* 110:923-932.

Sarafidis, P. A., P. C. Stafylas, P. I. Georgianos, A. N. Saratzis, and A. N. Lasaridis. 2010. Effect of thiazolidinediones on albuminuria and proteinuria in diabetes: a meta-analysis. *Am J Kidney Dis* 55:835-847.

Sato, H., S. Ishihara, K. Kawashima, N. Moriyama, H. Suetsugu, H. Kazumori, T. Okuyama, M. A. Rumi, R. Fukuda, N. Nagasue, and Y. Kinoshita. 2000. Expression of peroxisome proliferator-activated receptor (PPAR) gamma in gastric cancer and inhibitory effects of PPAR-gamma agonists. *Br J Cancer* 83:1394-1400.

Scoditti, E., M. Massaro, M. A. Carluccio, A. Distante, C. Storelli, and R. De Caterina. 2010. PPARgamma agonists inhibit angiogenesis by suppressing PKCalpha and CREB-mediated COX-2 expression in the human endothelium. *Cardiovasc Res* 86:302-310.

Straus, D. S., and C. K. Glass. 2007. Anti-inflammatory actions of PPAR ligands: new insights on cellular and molecular mechanisms. *Trends Immunol* 28:551-558.

Thorner, P. S., M. Ho, V. Eremina, Y. Sado, and S. Quaggin. 2008. Podocytes contribute to the formation of glomerular crescents. *J Am Soc Nephrol* 19:495-502.

Yang, H. C., S. Deleuze, Y. Zuo, S. A. Potthoff, L. J. Ma, and A. B. Fogo. 2009. The PPARgamma agonist pioglitazone ameliorates aging-related progressive renal injury. *J Am Soc Nephrol* 20:2380-2388.

Yang, H. C., L. J. Ma, J. Ma, and A. B. Fogo. 2006. Peroxisome proliferator-activated receptor-gamma agonist is protective in podocyte injury-associated sclerosis. *Kidney Int* 69:1756-1764.

Yang, J., Y. Zhou, and Y. Guan. 2012. PPARgamma as a therapeutic target in diabetic nephropathy and other renal diseases. *Curr Opin Nephrol Hypertens* 21:97-105.

Zuo, Y., H. C. Yang, S. A. Potthoff, B. Najafian, V. Kon, L. J. Ma, and A. B. Fogo. 2012. Protective effects of PPAR-gamma agonist in acute nephrotic syndrome. *Nephrol Dial Transplant* 27:174-181.

The invention claimed is:

1. A method of treating rapidly progressive glomerulonephritis in a subject in need thereof, comprising the step of administering to said subject a compound which is selected from the group consisting of PPARγ agonist or PPARγ expression activator.

2. The method according to claim 1 wherein said PPARγ agonist is Pioglitazone.

3. A method of promoting podocyte cell survival in a subject in need thereof, comprising the step of administering to said subject a compound which is selected from the group consisting of PPARγ agonist or PPARγ expression activator.

4. The method according to claim 3 wherein said PPARγ agonist is Pioglitazone.

5. The method according to claim 3 wherein said subject has rapidly progressive glomerulonephritis.

* * * * *